United States Patent [19]

Hoffman

[11] Patent Number: 4,731,053

[45] Date of Patent: Mar. 15, 1988

[54] CONTAINER DEVICE FOR SEPARATELY STORING AND MIXING TWO INGREDIENTS

[75] Inventor: James P. Hoffman, Blue Bell, Pa.

[73] Assignee: Merck & Co., Inc., Rahway, N.J.

[21] Appl. No.: 945,749

[22] Filed: Dec. 23, 1986

[51] Int. Cl.[4] .................... A61M 37/00

[52] U.S. Cl. .................... 604/89; 604/410; 206/221

[58] Field of Search .................... 604/89, 91, DIG. 25, 604/408-410, 262, 56, 416; 206/219, 221; 222/105

[56] References Cited

U.S. PATENT DOCUMENTS

| | | | |
|---|---|---|---|
| 2,176,923 | 10/1939 | Nitardy . | |
| 2,404,316 | 7/1946 | Sack . | |
| 2,580,836 | 1/1952 | Rausch . | |
| 2,663,298 | 12/1953 | Rose . | |
| 2,848,995 | 8/1958 | Ryan . | |
| 3,042,086 | 7/1962 | Winchell | 604/408 |
| 3,058,313 | 10/1962 | Robbins . | |
| 3,082,867 | 3/1963 | Gelpey | 206/221 |
| 3,149,943 | 9/1964 | Amador . | |
| 3,257,072 | 6/1966 | Reynolds . | |
| 3,276,447 | 10/1966 | Hamilton | 128/DIG. 24 |
| 3,290,017 | 12/1966 | Davies et al. . | |
| 3,462,070 | 8/1969 | Corella | 206/221 |
| 3,532,254 | 10/1970 | Burke . | |
| 3,545,671 | 12/1970 | Ross . | |
| 3,911,918 | 10/1975 | Turner | 604/410 |
| 3,950,158 | 4/1976 | Gossett | 206/219 |

*Primary Examiner*—C. Fred Rosenbaum
*Assistant Examiner*—H. Macey
*Attorney, Agent, or Firm*—Richard E. L. Henderson; Hesna J. Pfeiffer

[57] ABSTRACT

The present invention relates to a container device that is useful for separately storing two ingredients, typically a solid ingredient and a liquid ingredient, and subsequently mixing the two ingredients within the container device. The container device is especially useful for the storage of a solid ingredient that can be degraded during storage, by moisture, and a liquid ingredient wherein, when such ingredients are mixed, the mixture is stable for only a short period of time.

4 Claims, 6 Drawing Figures

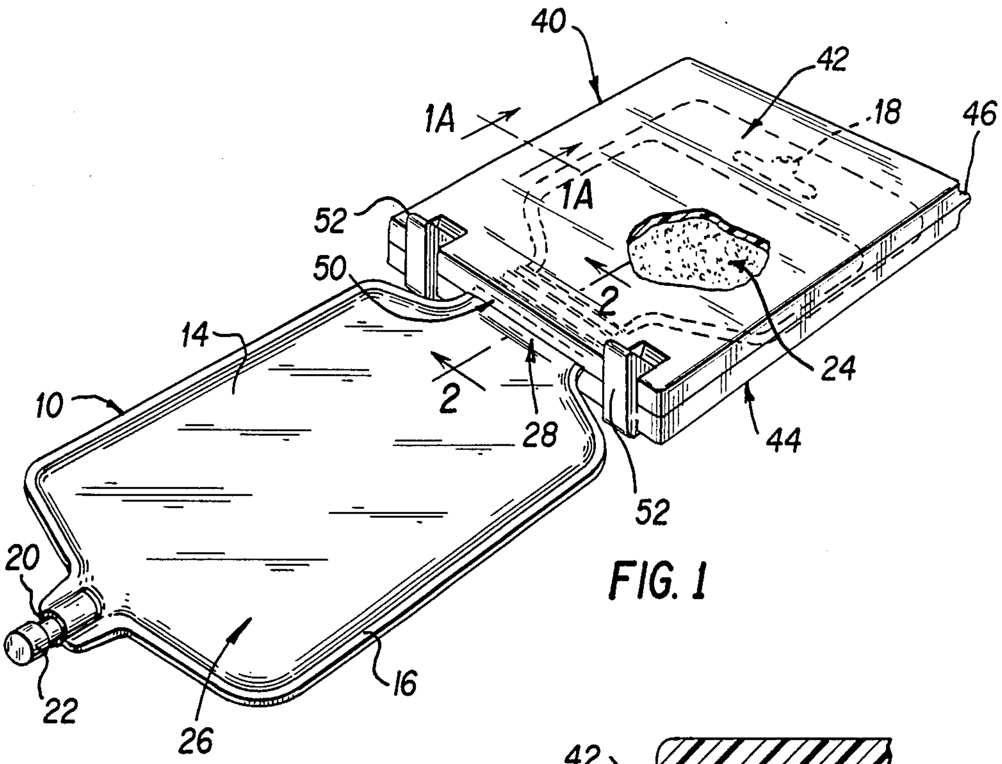
FIG. 1
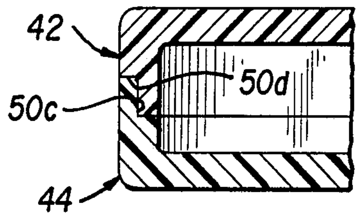
FIG. 1A
FIG. 2
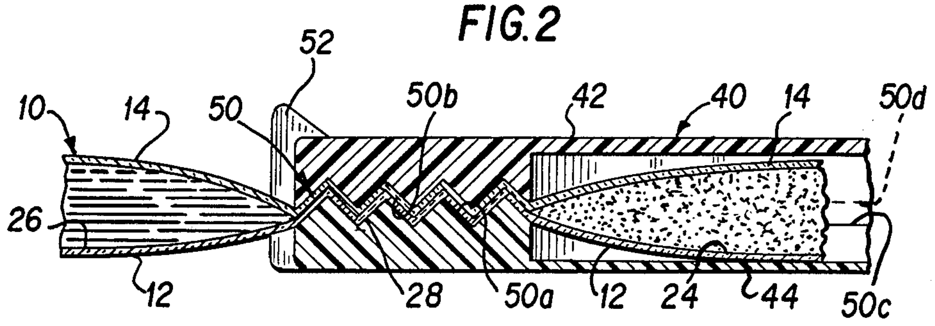

CONTAINER DEVICE FOR SEPARATELY STORING AND MIXING TWO INGREDIENTS

BACKGROUND OF THE INVENTION

The present invention relates to a container device that is useful for separately storing two ingredients, typically a solid ingredient and a liquid ingredient, and subsequently mixing the two ingredients within the container device. The container device is especially useful for the storage of a solid ingredient that can be degraded during storage, by moisture, and a liquid ingredient wherein, when such ingredients are mixed, the mixture is stable for only a short period of time. For example, a major use of such a container device is for the storage of two intravenous ingredients, eg. a hygroscopic powdered medicament and a liquid diluent. More particularly, the present invention relates to a container device that comprises a flexible bag and an encapsulating container wherein the encapsulating container encapsulates a portion of the flexible bag. The encapsulating container has releasable partitioning means. The releasable partitioning means has three functions: (i) to form a first compartment which comprises the encapsulated portion of the flexible bag, which contains the solid ingredient, and a second compartment which comprises the nonencapsulated portion of the flexible bag, which contains the liquid ingredient; (ii) to seal the encapsulated portion of the flexible bag from the atmosphere external to the encapsulating container; and (iii) to secure the encapsulating container to the flexible bag. Upon release of the releasable partitioning means, the encapsulating container can be removed and the solid ingredient and the liquid ingredient can be mixed.

Container devices that provide separate spaces in a single unit for separately storing two ingredients that can then be mixed within the container device are known. For example, U.S. Pat. Nos. 4,396,383, 3,545,671 and 3,257,072 disclose multi-compartment flexible bags for the storage and subsequent mixing of two liquid ingredients. These designs, perhaps ideal for the storage of two liquid ingredients, may not be suitable when at least one of the ingredients is a solid component that can be degraded by moisture.

Some solid ingredients, such as a hygroscopic medicament, can easily be degraded by moisture when stored in a multi-compartment flexible bag. It is believed that moisture can attack the solid ingredient from three paths. First, moisture from the liquid ingredient can leak through the partition separating the solid ingredient from the liquid ingredient. Second, atmospheric moisture can penetrate the flexible bag. Third, which is somewhat related to the first and second, moisture emanating from the liquid ingredient can penetrate the flexible bag to the atmosphere and then repenetrate the flexible bag where the solid ingredient is stored. The third path is of particular concern if the compartment of the flexible bag that contains the solid ingredient and the compartment of the flexible bag that contains the liquid ingredient are stored in the same container or are in contact with each other during storage.

The liability of utilizing a multicompartment flexible bag to store a solid ingredient is appreciated in the art. U.S. Pat. No. 4,467,588 discloses a container system for separately storing a sterilized powder and a sterilized liquid in a container device. The container system includes two sealed chambers having a sterilized frangible connection therebetween, one said chamber containing the liquid ingredient and the other said chamber including a sealed vial containing a solid ingredient. A similar container device, which is used for the storage of a powdered medicament and a liquid diluent, is being marketed by Abbott Laboratories under the tradename ADD Vantage.

These devices, although perhaps rendering stability to the solid ingredient, have many drawbacks. One drawback is that such devices have numerous components, many of which must be sterilized. The vial, the flexible bag and all the components connecting them must be sterilized. Sterilization, especially the maintenance of sterility of each component during the period of time that the solid ingredient and liquid ingredient are being placed in the container, is very expensive. Another drawback is that at the joints connecting the vial and flexible bag there is the opportunity for microbial attack, which may result in the end user getting an infection. Yet another drawback is that in order to mix the contents of the vial and flexible bag, a frangible connector must be broken. This results in a portion of the frangible connector being placed in the flexible bag. The patient receiving the solution may find this disturbing. Also, during mixing, some of the solid ingredient can get caught in the joints connecting the vial and flexible bag. Not only is such solid ingredient wasted, but also this may render the entire mixture useless. Yet another drawback is that when such container device is being utilized, the vial is present. In view of that the vial is typically glass, there exists the possibility that it can break. Still another drawback is that someone other than the manufacturer will typically connect the vial and flexible bag. Thus, there is the possibility that one may connect the wrong vial and flexible bag.

Accordingly, there is the need for a container device that can separately store a solid ingredient and liquid ingredient without the solid ingredient being degraded during storage and yet, such two ingredients can be mixed easily in the container device and not have the drawbacks described hereinabove.

SUMMARY OF THE INVENTION

The container device of the present invention provides a system for separately storing and subsequently mixing within the container device a solid ingredient that can be degraded, during storage by moisture, eg. a powdered hygroscopic medicament, and a liquid ingredient, such as a diluent. The container device comprises two components. The first component is a flexible bag. The liquid ingredient and solid ingredient are stored separately in the flexible bag. The second component is an encapsulating container that encapsulates a portion of the flexible bag. In a preferred embodiment, the encapsulating container is made of a rigid material. The encapsulating container also comprises releasable partitioning means.

The releasable partitioning means has three functions: (i) to form a first compartment which comprises the encapsulated portion of the flexible bag, which contains the solid ingredient, and a second compartment which comprises the nonencapsulated portion of the flexible bag, which contains the liquid ingredient; (ii) to seal the encapsulated portion of the flexible bag from the atmosphere external to the encapsulating container; and (iii) to secure the encapsulating container to the flexible bag. The formation of such two compartments keeps the contents of the first compartment from contacting the contents of the second compartment and vice-versa. Thus, prior to use, the solid ingredient is separated from the liquid ingredient and is also protected from atmospheric moisture, thus permitting the solid ingredient to maintain its integrity during storage. Upon release of the releasable partitioning means, the encapsulating container can be removed and the solid ingredient and the liquid ingredient can be mixed within the container device. The flexible bag can now be utilized for its intended end use.

This simple and economical container device provides numerous benefits. Many of the benefits are derived from the fact that only the flexible bag contacts the liquid ingredient and solid ingredient. Prior to use, the solid ingredient is protected from atmospheric moisture and separated from the liquid ingredient by the encapsulating container, which never contacts the contents of the flexible bag. This means that, for medical use, for example, only the flexible bag need be sterilized during production and filling; the encapsulating container need not be sterilized. There are no separate connecting components that are utilized to join the solid ingredient and liquid ingredient, thus there is virtually no possibility for microbial attack. The solid ingredient and liquid ingredient can be mixed thoroughly; there is virtually no chance of the solid ingredient being hidden from view by being caked on some connecting component. Yet another benefit is that during use only the flexible bag is present and, therefore, no breakable components are present. Still another benefit of the invention is that the encapsulating container is reusable, which reduces the cost of the container device of the invention. Also, since the encapsulating container protects the solid ingredient from atmospheric moisture and separates the solid ingredient and liquid component, the flexible bag can be made of standard, inexpensive material. Such a material permits one to visualize the contents of the flexible bag in order to determine whether or not the mixing is adequate, in terms of completeness of mixing, color, clarity, freedom from particulate matter and other characteristics whose evaluation is mandated by, for example, Food and Drug Admininistration-approved labeling for intravenous solutions of certain medications for human use.

DESCRIPTION OF THE DRAWINGS

FIG. 1 is a perspective view of the container device of the invention.

FIG. 1A is a cross-sectional view through the releasable partitioning means taken along line 1A—1A of FIG. 1.

FIG. 2 is a cross-sectional view of the releasable partitioning means taken along line 2—2 of FIG. 1.

Proceeding to a detailed description of the preferred embodiment of the invention, FIGS. 1 through 3 show a flexible bag, generally 10, and an encapsulating container, generally 40. Flexible bag 10 can be utilized for the storage of a solid ingredient and a liquid ingredient, with the solid ingredient being stored in upper portion 24 of flexible bag 10 and the liquid ingredient being stored in lower portion 26 of flexible bag 10. As can be seen in FIG. 1, encapsulating container 40 encapsulates a portion of flexible bag 10. This results in encapsulating container 40, via releasable partitioning means 50, separating flexible bag 10 into two compartments at neck portion 28 of flexible bag 10, one being upper portion 24 and the other being lower portion 26. Typically, neck portion 28 contains neither the solid ingredient nor the liquid ingredient. Also, encapsulating container 40, via releasable partitioning means 50, seals upper portion 24 from the atmosphere external to encapsulating container 40 and secures encapsulating container 40 to flexible bag 10. It is believed that the solid component will remain stable for a period of at least several months.

As can be seen in FIG. 3, flexible bag 10 is characterized by being formed from two flexible transparent sheets 12 and 14 of a flexible material that are joined at their respective perimeters to form edge 16. At the top of the flexible bag 10 is hanger portion 18. Hanger portion 18 is utilized to hang flexible bag 10 on a stand at the time when the contents of the flexible bag 10, having been mixed, are to be administered to a patient. It should be noted that a benefit of this embodiment of theinvention is that hanger portion 18 is not capable of being utilized until encapsulating container 40 is separated from flexible bag 10, thus eliminating, in human medical use, the nursing error of hanging a flexible bag without having added the solid ingredient or without having mixed the solid ingredient and liquid ingredient. Referring to FIG. 1, port 20 is used to connect flexible bag 10 to an intravenous system, once the cap 22 is removed.

Figure 3:
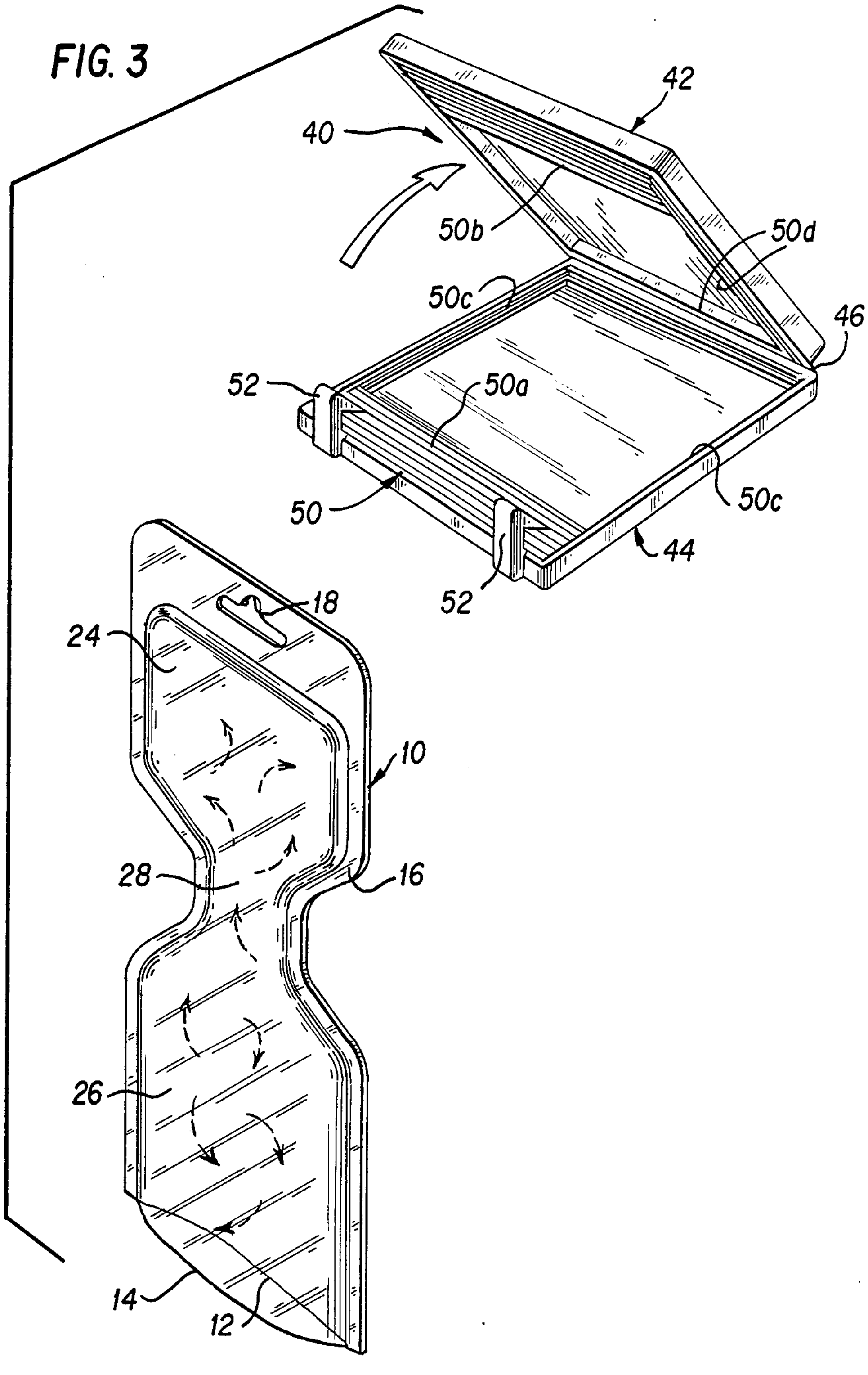
FIG. 3 is an exploded perspective view of the encapsulating container and flexible bag of FIG. 1.

As can be seen in FIG. 3, is the encapsulating container 40 in the open position. Encapsulating container 40 is preferred because it is one component. The encapsulating container 40 has a lid 42 and body portion 44 whereby lid 42 is attached to body portion 44 by an integrally formed hinge 46. Lid 42 can rotate about hinge 46, which permits lid 42 to open and close. Along the upper surface edge of body portion 44 and the lower surface edge of lid 42 is releasable partitioning means, generally 50. Body portion 44 has releasable partitioning means 50*a* and 50*c* and lid 42 has releasable partitioning means 50*b* and 50*d*. Releasable partitioning means 50*a* and 50*b* are grooved. As can be seen in FIG. 1, such grooves are useful to prevent the contents of upper portion 24 and the contents of lower portion 26 from contacting each other and to secure flexible bag 10 to encapsulating container 40. Releasable partitioning means 50*a*, 50*b*, 50*c* and 50*d* contribute to keeping atmospheric moisture from entering encapsulating container 40. Body portion 44 also comprises clips 52. When lid 42 is closed, clips 52 deflect outwardly and then return to their original position to maintain lid 42 tightly compressed against body portion 44.

The container device of the invention is obtained by placing the upper portion 24 in body portion 44 with neck portion 28 being wedged between the releasable partitioning means 50*a* and 50*b* by closure of lid 42.

The contents of flexible bag 10 can be mixed by opening encapsulating container 40 by lifting lid 42 and removing encapsulating container 40 and forcing the contents, by squeezing, of lower portion 26 through neck portion 28 and into the upper portion 24 and vice-versa. The contents of flexible bag 10 are now ready to be utilized. Also, encapsulating container 40 can now be reused with a new flexible bag 10.

Figure 4:
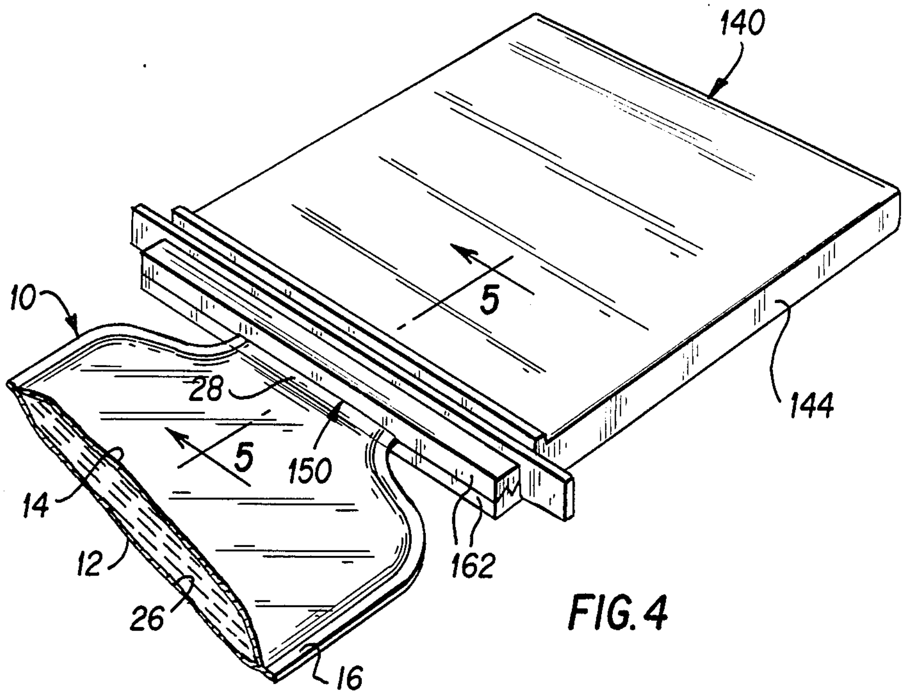
FIG. 4 is a perspective view of an alternative embodiment of the container device of the invention.
Figure 5:
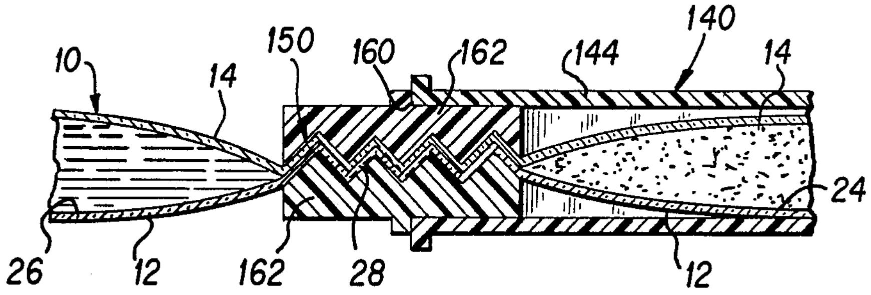
FIG. 5 is a cross-sectional view of the releasable partitioning means taken along line 5—5 of FIG. 4.

FIGS. 4 and 5 depict an alternative embodiment of the container device of the invention wherein the same reference numerals with a prefix of 100 have been employed to designate parts of the encapsulating container having the same general function as the encapsulating container in the preferred embodiment. Encapsulating container 140 is less preferred than encapsulating container 40 because encapsulating container 140 is made of three components- body portion 144 and two strips 162, albeit when in use encapsulating container 140 is one integral unit. Encapsulating container 140 has no lid 42, but rather body 144 is one unit which is open along edge 160. Two strips 162 interfit within the opening like a hand and glove. The surfaces of strips 162 that contact each other are releasable partitioning means 150. Releasable partitioning means 150 is grooved in order to prevent the contents of upper portion 24 from contacting the contents of lower portion 26 and to secure flexible bag 10 to encapsulating container 140. Flexible bag 10 can be placed in encapsulating container 140 by removing strips 162 and placing neck portion 28 of flexible bag 10 between releasable partitioning means 150. Strips 162, with upper portion 24 of flexible bag 10 being placed inside body portion 144 of encapsulating container 140, are then returned to body portion 144 of encapsulating container 140. Flexible bag 10 can be removed from encapsulating container 140 by simply removing strips 162 from body portion 144 and then separating strips 162, which permits one to mix the contents of flexible bag 10.

Flexible bag 10 can be filled by virtually any technique. However, a very simple method is as follows. A portion of edge 16 of upper portion 24 of flexible bag 10 is kept unsealed. A temporary clamp is placed over the neck portion 28 in order to prevent the contents of upper portion 24 from entering lower portion 26. The solid ingredient is now inserted into such unsealed portion of edge 16. Edge 16 can now be sealed by, for example, heat. Flexible bag 10 is now placed in encapsulating container 40 to form the container device of the invention. The temporary clamp is now removed. The lower portion 26 of flexible bag 10 can now be filled. This can be carried out by leaving a portion of edge 16 of lower portion 26 unsealed, then filling lower portion 26 with the liquid ingredient and then sealing such edge 16. Alternatively, lower portion 26 could be filled through administration port 20. It should be noted that no temporary clamp is needed because encapsulating container 40 is secured to flexible bag 10.

Flexible bag 10 can be made of essentially any nonrigid material that can store the desired solid ingredient and liquid ingredient. It is preferred that the material be transparent, which permits one to evaluate easily the color, clarity, stability or other characteristics of the contents of flexible bag 10. Suitable materials are flexible plastics such as polyethylene, and polypropylene.

Encapsulating container 40 can be made from any suitable material that is capable of preventing moisture from penetrating flexible bag 10. A flexible material can be utilized, such as those materials of flexible bag 10. It is preferred that encapsulating container 40 be rigid. Suitable rigid materials include polycarbonate, high density polyethylene, metal and glass, although glass is less preferred because of the potential for breakage. Also, if the solid ingredient can be degraded by light, then it is preferred that the material be nontransparent, eg. opaque. It should be noted that releasable partitioning means **50*a* and 50*b* need not be grooved, but could be otherwise patterned or not patterned so long as releasable partioning means 50*a* and 50*b* can prevent the contents of lower portion 26 and upper portion 24 from contacting each other and can secure flexible bag 10 to encapsulating container 40**.

The container device can be utilized to store not only a powdered medicament and a diluent but also any two components that are stable for only a short period of time upon mixing, especially when one of such components is susceptible to degradation, during storage by moisture. For example, the container device can be utilized to store dehydrated food and water or even two liquid components.

The foregoing invention can now be practiced by those skilled in the art. Such skilled persons will know that the invention is not necessarily restricted to the particular embodiments described herein. The scope of the invention is to be defined by their terms of the appended claims, which are given meaning by the preceding description.

What is claimed is:

1. A device for separately storing two ingredients and subsequently mixing said ingredients in said device comprising:

(A) a flexible bag; and (B) an encapsulating container, wherein said encapsulating container:

(a) encapsulates a portion of said flexible bag; and (b) comprises releasable partitioning means for: forming a first compartment comprising said encapsulated portion of said flexible bag and a second compartment comprising said non-encapsulated portion of said flexible bag, sealing said first compartment from the atmosphere external to said encapsulating container ; and securing said encapsulating container to said flexible bag, wherein upon the release of said releasable partitioning means said encapsulating container is no longer secured to said flexible bag.

2. The device of claim 1 wherein said second compartment comprises at least one port.

3. The device of claim 2 wherein said encapsulating container is made of a rigid material.

4. The device of claim 3 wherein said encapsulating container is one component.

* * * * *